(12) United States Patent
Harvey et al.

(10) Patent No.: US 7,748,283 B2
(45) Date of Patent: Jul. 6, 2010

(54) CONTROLLED TRANSFER BIOLOGICAL SAMPLE COLLECTION DEVICES AND METHODS OF USING SUCH DEVICES

(75) Inventors: Michael A. Harvey, Spofford, NH (US); Breck O. Parker, Saco, ME (US); Stevan P. Tortorella, Wells, ME (US); Elizabeth A Moran, Randolph, NJ (US); John Pipinias, Eliot, ME (US)

(73) Assignee: Whatman, Inc., Florham Park, NJ (US)

( * ) Notice: Subject to any disclaimer, the term of this patent is extended or adjusted under 35 U.S.C. 154(b) by 509 days.

(21) Appl. No.: 11/707,313

(22) Filed: Feb. 16, 2007

(65) Prior Publication Data
US 2008/0196517 A1   Aug. 21, 2008

(51) Int. Cl.
*B01L 3/00* (2006.01)
(52) U.S. Cl. ................. 73/864.91; 422/102
(58) Field of Classification Search .......... 73/864.32, 73/864.31, 864.91
See application file for complete search history.

(56) References Cited

U.S. PATENT DOCUMENTS

| | | | | |
|---|---|---|---|---|
| 4,789,629 A | * | 12/1988 | Baker et al. | 435/7.92 |
| 5,308,580 A | * | 5/1994 | Clark | 422/58 |
| 5,418,142 A | * | 5/1995 | Kiser et al. | 435/14 |
| 5,756,126 A | | 5/1998 | Burgoyne | 424/488 |
| 5,939,259 A | | 8/1999 | Harvey et al. | 435/6 |
| 5,972,386 A | | 10/1999 | Burgoyne | 424/488 |
| 5,976,572 A | | 11/1999 | Burgoyne | 424/488 |
| 5,980,828 A | * | 11/1999 | McClintock et al. | 422/58 |
| 6,168,922 B1 | | 1/2001 | Harvey et al. | 435/6 |
| 6,294,203 B1 | | 9/2001 | Burgoyne | 424/488 |
| 6,447,804 B1 | | 9/2002 | Burgoyne | 424/488 |
| 6,627,226 B2 | | 9/2003 | Burgoyne et al. | 424/488 |
| 7,488,450 B2 | | 2/2009 | Matusewicz et al. | 422/58 |
| 2001/0039057 A1 | * | 11/2001 | Douglas et al. | 436/169 |
| 2005/0196318 A1 | | 9/2005 | Matusewicz et al. | 422/58 |
| 2005/0227269 A1 | * | 10/2005 | Lloyd et al. | 435/6 |
| 2006/0057738 A1 | * | 3/2006 | Hall | 436/177 |
| 2006/0246598 A1 | | 11/2006 | Dai et al. | 436/169 |

FOREIGN PATENT DOCUMENTS

| | | |
|---|---|---|
| WO | WO-90/13819 | 11/1990 |
| WO | WO-03/050507 | 6/2003 |
| WO | WO-2005/087376 | 9/2005 |
| WO | WO-2006/042004 | 4/2006 |

* cited by examiner

*Primary Examiner*—Hezron Williams
*Assistant Examiner*—Tamiko D Bellamy
(74) *Attorney, Agent, or Firm*—Edwards Angell Palmer & Dodge LLP; David G. Conlin, Esq.; Kathryn A. Piffat, Esq.

(57) ABSTRACT

The field of the present invention pertains to a controlled transfer biological collection device using a dry solid storage and transfer medium and a method for the collection of biological material of interest (genetic or proteinaceous material) in a form suitable for storage and/or subsequent analysis. Specifically, the present invention provides for a sampling device that controls the transfer of the biological sample to the storage medium by holding the storage medium and a moveable sample collection member having an analyte collection surface. The invention further provides for a method not only for storing a biological analyte on this collection device but also for analyzing the stored biological analyte using methods that are suited for automated analyzing systems.

31 Claims, 4 Drawing Sheets

SECTION B-B

SECTION A-A

CONTROLLED TRANSFER BIOLOGICAL SAMPLE COLLECTION DEVICES AND METHODS OF USING SUCH DEVICES

BACKGROUND OF THE INVENTION (1) Field of the Invention

The field of the present invention pertains to a controlled transfer biological collection device using a dry solid storage and transfer medium and a method for the collection of biological material of interest (genetic or proteinaceous material) in a form suitable for storage and/or subsequent analysis. Specifically, the present invention provides for a sampling device that controls the transfer of the biological sample to the storage medium by holding the storage medium and a moveable sample collection member having an analyte collection surface. The invention further provides for a method not only for storing a biological analyte on this collection device but also for analyzing the stored biological analyte using methods that are suited for automated analyzing systems.

(2) Description of the Related Art, Including Information Disclosed Under 37 CFR 1.97 & 1.98

The collection of biological samples (such as blood) and extracting DNA for genetic analysis from the sample has been widely used by the forensics and medical community for identification purposes, for paternity testing, for genetic diagnostic testing in new born screening programs, for genetic typing for predisposition to disease and for genetic characterization for drug susceptibility. However, due to the invasive nature of blood collection, alternative non-invasive methods are coming into favor. Current methods involve scraping cellular mucosa from inside the oral cavity using any of a number of different devices such as cytobrushes, cotton or Dacron swabs, mouthwash swish and rinse methods, foam tipped swabs, and supported cellulosic filter paper collection techniques (known as the Bode method). These methods require time-consuming, labor intensive extraction methods.

The introduction of treated storage matrices into the forensics community has significantly streamlined the collection and extraction of DNA from a variety of samples. The use of FTA® brand treated matrices (from Whatman, Inc. of Florham Park, N.J. USA) with non-invasive buccal cell collection techniques presents a new set of problems. With the use of conventional buccal swabs, one can fail to transfer buccal cells to the treated matrix in a consistent and reproducible manner. If the swab used to collect the sample is separate and distinct from the treated matrix receiving the sample, then forensic traceability issues arise, particularly if the two become separated later in the chain of custody of forensic evidence.

Examples of treated matrices for biological sample collection or storage and associated collection devices can be found in the following US patents: U.S. Pat. No. 6,627,226, U.S. Pat. No. 6,447,804, U.S. Pat. No. 6,294,203, U.S. Pat. No. 6,168,922, U.S. Pat. No. 5,976,572, U.S. Pat. No. 5,972,386, U.S. Pat. No. 5,939,259, and U.S. Pat. No. 5,756,126. Basically, these patents use two different methodologies for stabilizing biological samples.

The first stabilizing method uses a combination of an absorbent material as a storage medium that does not bind to nucleic acids and a chaotropic salt impregnated about the storage medium. (For the purposes of the cited prior art and the present invention, "chaotropic salts" include any substance capable of altering the secondary, tertiary, or quaternary structure of biomolecules in aqueous solution, but leaves the primary structure intact.) Preferably, a chaotropic salt is said to inactivate any nucleic acid amplification inhibitors present in the biological source, by precipitation, by inducing the inhibitor to irreversibly bind to the matrix, or by causing substantially irreversible denaturation of the inhibitor. Suitable chaotropic salts include guanidinium salts such as guanidine isothiocyanate, guanidine thiocyanate, guanidine hydrochloride, sodium iodide, sodium perchlorate, potassium iodide, sodium isothiocyanate, urea, or combinations thereof.

The second stabilizing method also uses a dry solid storage medium but a different adsorbed or absorbed stabilizer. Here, the protectant composition comprises a protein denaturing agent (such as an anionic detergent) and a free radical trap (such as a weak base, and a chelating agent, and optionally, uric acid or a urate salt).

BRIEF SUMMARY OF THE INVENTION

The present invention relates to a controlled transfer biological collection device using a dry solid storage and transfer medium and a method for the collection of biological material of interest (genetic or proteinaceous material) in a form suitable for storage and/or subsequent analysis.

The present collection device for a biological sample that contains degradable biologically sourced analytes comprises three elements. A moveable sample collection member is one element and is equipped with an analyte collection surface that, preferably, has the ability to absorb more sample than is necessary for transfer to a storage medium. A storage medium suitable for collecting and storing the biological sample is held in place by a storage medium holder. The holder not only keeps the operator's fingers away from the storage transfer location, but also provides a holding means for holding the storage medium in a fixed position and for applying contact pressure between the storage medium and the analyte collection surface. The holder also has a means for holding the moveable sample collection member. Thus, the two elements, the storage medium and the analyte collection surface are held together for traceability purposes.

Functionally, the moveable sample collection holding means allows the moveable collection member, and its analyte collection surface, to move between a first open position for collecting the biological sample on the analyte collection surface prior to sample collection and a second closed position facing or contacting at least a portion of the storage medium after collection and transfer of the sample. For the purposes of the present invention, the term "surface" refers to more than a two-dimensional space, including volume as well. Thus, a "surface" can be the volume of a foam pad, for example, and not just its contact surface area.

In use, one takes the above described device and contacts the analyte collection surface with the biological sample. The moveable collection member is moved towards the storage medium such that the analyte collection surface and the storage medium are brought in contact, allowing the transfer of the biological sample to the storage medium. In preferred embodiments, one engages the holding means on the storage medium holder in doing so, thereby allowing the analyte collection surface to be held facing the storage medium after the transfer is complete.

For analysis of the biological sample, the storage medium is manipulated so as to remove at least a portion of the biologically sourced analyte present on the storage medium.

Examples of storage media suitable for the present invention include untreated filter paper, such as #903® brand paper (Whatman, Inc., Florham Park, N.J. USA) or treated filter papers, such as FTA and FTA Elute brand paper (also from Whatman, Inc., Florham Park, N.J. USA). These treated matrices are described in US patents referenced above. Such treated matrices provide a simple safe method for collection, shipping and storage of biological samples. They also contain chemistries which make it easy to isolate DNA from complex samples such as blood. Samples collected on treated or untreated matrices are dried for storage and can be stored at room temperature for long periods of time.

An object of the invention is to provide a controlled transfer of a biological sample to a dry, treated solid storage and transfer medium, such as providing a reproducible pressure or movement between the analyte collection surface and the storage medium.

A second object of the invention is to provide a device or method that has a spare sample source in sample retained in an absorbent analyte collection surface.

A third object of the invention is to provide a device or method that retains the sample collector surface and the storage medium together for chain of custody traceability purposes.

A fourth object of the invention is to provide a device or method in which the storage medium can be processed by automated analyzing methods.

A fifth object of the invention is to provide a device or method for the long term storage for biological samples.

DETAILED DESCRIPTION OF THE INVENTION

Figure 1:
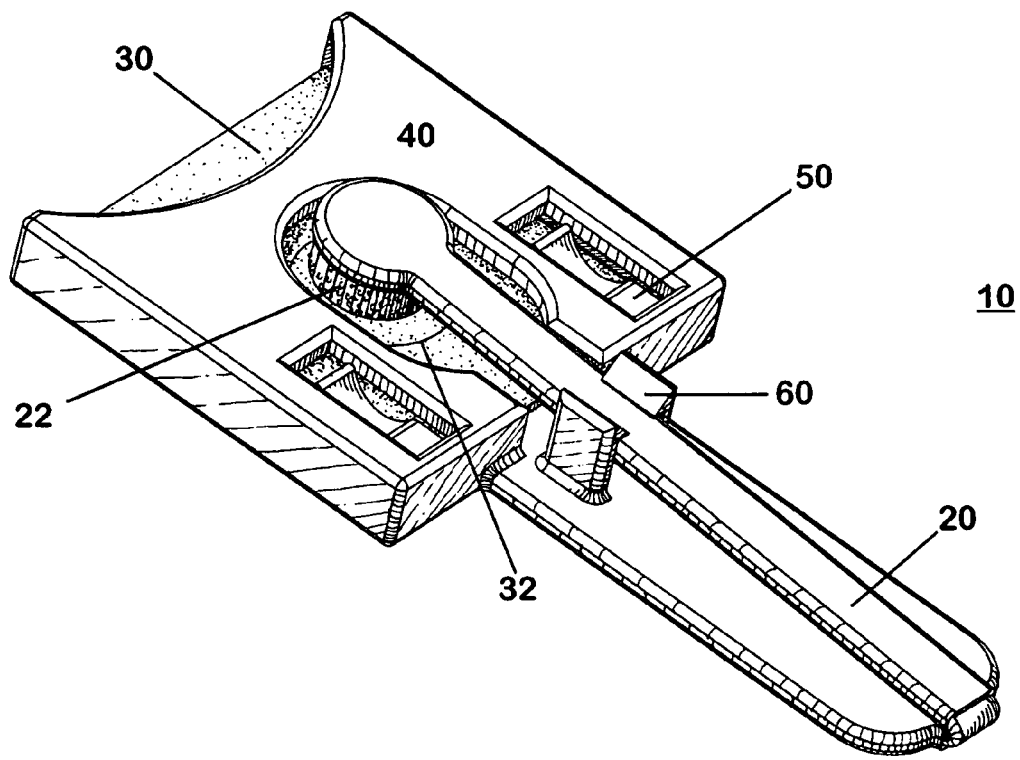
FIG. 1 is a perspective view of a preferred embodiment of the present invention showing the claimed element in a closed position.
Figure 2:
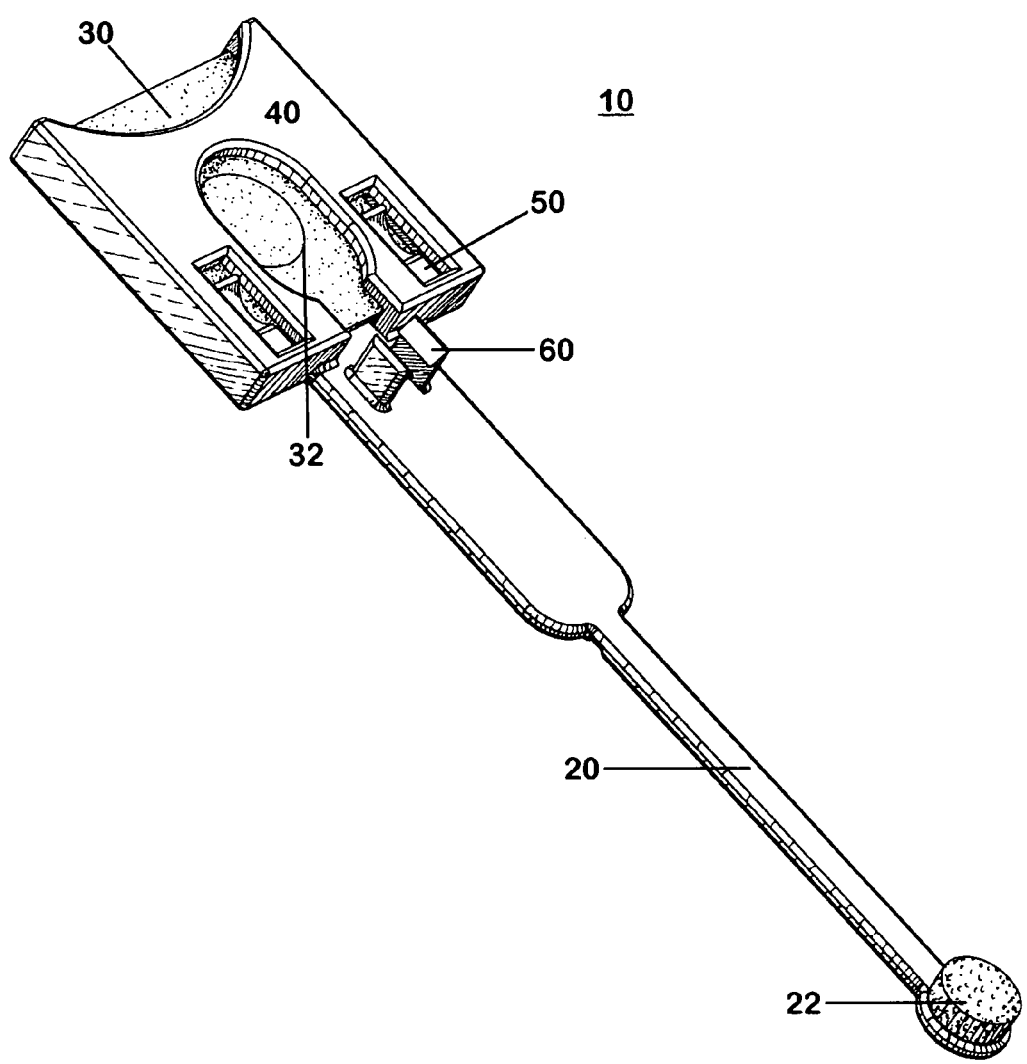
FIG. 2 is a perspective view of a preferred embodiment of the present invention showing the claimed element in an open position.
Figure 3:
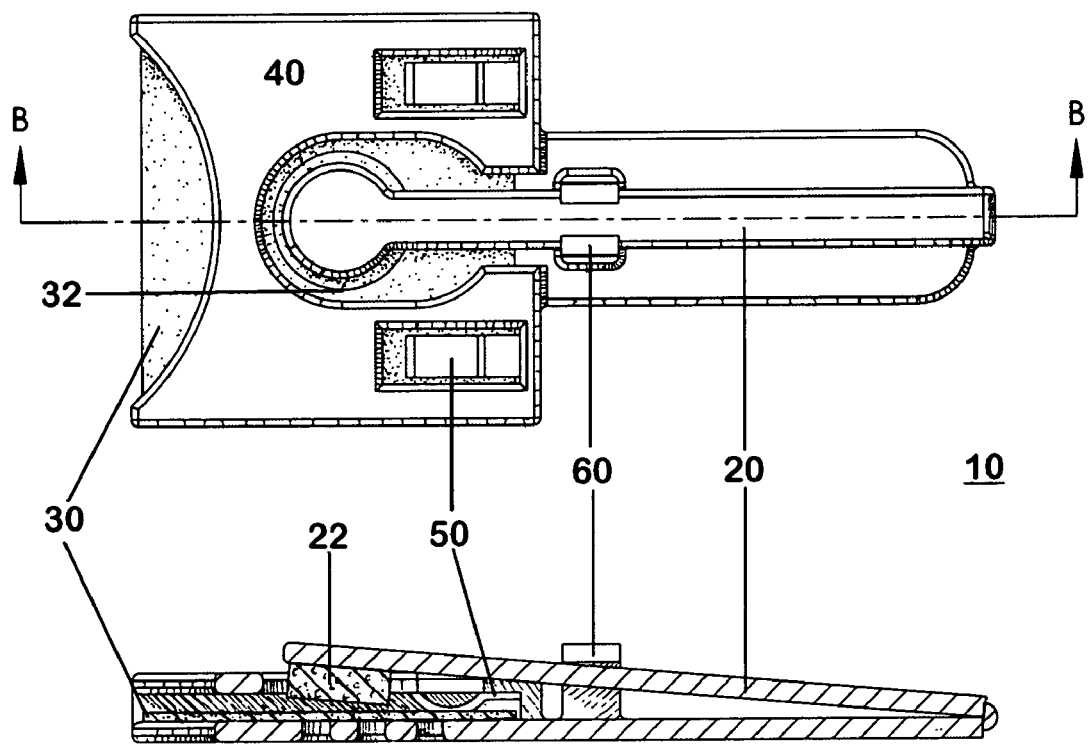
FIG. 3 is a plan and sectional view of the FIG. 1 device.
Figure 4:
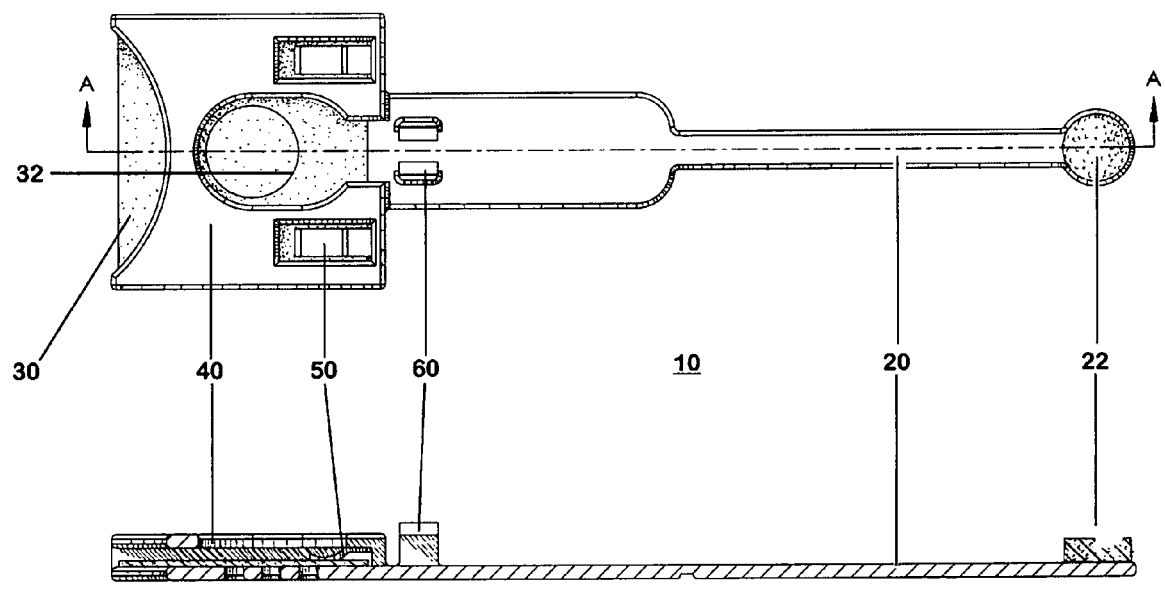
FIG. 4 is a plan and sectional view of the FIG. 2 device.

A preferred embodiment is shown in FIG. 1. The collection device (10) for a biological sample that contains degradable biologically sourced analytes comprises a moveable sample collection member (20) having an analyte collection surface (22), a storage medium (30), and a storage medium holder (40) having a means for holding the storage medium in a fixed position (50) and a means (60) for holding the moveable sample collection member (20). The moveable sample collection holding means allows the moveable collection member surface to move either from a first closed position facing or contacting at least a portion of the storage medium (as shown in FIGS. 1 and 3) to a second open position for collecting the biological sample on the analyte collection surface (as shown in FIGS. 2 and 4) or vice versa.

Preferably, the means for holding the moveable sample collection member comprises a unitary connection between the storage medium holder and the moveable sample collection member (as shown in the FIGURES). Also preferably, the moveable sample collection surface is dimensioned and configured to be in spring tension away from the storage medium surface when held by the member holding means such that the analyte collection surface is held off the storage medium thereby allowing enough space for air drying of the storage medium after transfer of the sample to the storage medium from that surface.

Preferably the storage medium will also comprise at least one stabilizing reagent that preserves at least one biological sample analyte for transport or storage. Suitable such reagents include either the combination of a weak base, a chelating agent, and, optionally, uric acid or a urate salt or simply the addition of a chaotropic salt, alone or in combination with a surfactant. Also preferably, the storage medium will have a visual delineation (32) placed around the transfer area of the storage medium such that if removed from the storage holding means an operator can know where the material was deposited without reference to the device.

The present device can be used to collect degradable biologically sourced analytes such as nucleic acids, proteins, and respective fragments thereof. The biological sample can be selected from the group consisting of saliva, blood, serum, lymph fluids, buccal cells, mucosal cells, cerebrospinal fluid, semen, feces, plasma, urine, a suspension of cells, or a suspension of cells and viruses.

Preferably, the present device is dimensioned and configured such that the storage medium holder (40) releaseably holds the storage medium (30) in the fixed position by the holding means (50) (such as the plastic arms shown in the FIGURES). Thus, one can separate the storage medium from the storage holder for subsequent processing or storage. The tension on the storage medium should allow for manual or automated extraction, but not allow for accidental loss of the storage medium from the device. In some case, one can dimension and configure the storage medium holder so as to expose at least a portion of the storage medium for removal of the storage medium from the storage medium holder.

Preferably, the analyte collection surface (22) comprises an absorbent material, such as a conventional porous polyurethane foam pad (from Powell Products, inc. of Colorado Springs, Colo. USA), that is suitable for collecting a biological sample. The analyte collection surface should be dimensioned and configured such that the volume of sample is controlled. By controlling the volume, any stabilizing reagents on the storage medium aren't overloaded in their respective protecting capacity. If used in buccal swab applications, the pad should be dimensioned and configured to fit within the human mouth.

For record keeping and traceability the present device should also comprise an identification label (such as conventional bar coding) on not only the storage medium, but also the collection member, and if not unitary, the storage medium holder as well.

To ensure device integrity, the present device can also comprise a sterility envelope surrounding the other device elements. Preferably, those other elements are sterile and free from any biological sample analytes (made for example, from medical grade plastics), which can be done through conventional techniques such as irradiation after the envelope is sealed.

Kits can be made that incorporate the above device along with any combination of associated equipment or reagents including purification reagents, buffers, or the like and storage systems, containers, or the like.

Example of Device Use

The present device can be used for biological sample collection for the following purposes: the collection of buccal cell samples for criminal databases; the collection of crime scene samples (i.e., rehydrated blood, semen, saliva and liquid samples of the same); the collection of sexual assault samples; the collection of buccal samples for population genetics or pharmacogenomics studies; the collection of buccal samples for personal genetic ID archiving; the collection of bacterial or parasite samples from food sources; the collection of blood from meat at slaughterhouse for meat traceability; or the collection of biological samples from animals for veterinary diagnostics

We claim:

1. A collection device for a biological sample that contains degradable biologically sourced analytes comprising:
   a) a moveable sample collection member having an analyte collection surface;
   b) a storage medium wherein the storage medium comprises at least one stabilizing reagent that preserves at least one biological sample analyte for transport or storage; and
   c) a storage medium holder having a means for holding the storage medium in a fixed position and a means for holding the moveable sample collection member;
   wherein the moveable sample collection holding means allows the moveable collection member surface to move between a first open position for collecting the biological sample on the analyte collection surface and a second closed position facing or contacting at least a portion of the storage medium.

2. The device of claim 1 wherein the stabilizing reagent comprises a weak base and a chelating agent.

3. The device of claim 1 wherein the stabilizing reagent comprises a chaotropic salt.

4. The device of claim 1 wherein the degradable biologically sourced analytes include nucleic acids, proteins, and respective fragments thereof.

5. The device of claim 1 wherein the biological sample is selected from the group consisting of saliva, blood, serum, lymph fluids, buccal cells, mucosal cells, cerebrospinal fluid, semen, feces, plasma, urine, a suspension of cells, or a suspension of cells and viruses.

6. The device of claim 1 wherein the storage medium holder releaseably holds the storage medium in the fixed position, allowing the storage medium to be separated from the storage medium holder.

7. The device of claim 1 wherein the analyte collection surface is absorbent.

8. The device of claim 1 also comprising an identification label.

9. The device of claim 1 wherein the storage medium holder is dimensioned and configured to expose at least a portion of the storage medium for removal of the storage medium from the storage medium holder.

10. The device of claim 1 also comprising a sterility envelope surrounding the other device elements and those other elements are sterile and free from any biological sample analytes.

11. The device of claim 1 wherein the means for holding the moveable sample collection member comprises a unitary connection between the storage medium holder and the moveable sample collection member.

12. A method for collecting a biological sample that contains degradable biologically sourced analytes comprising:
   a) obtaining a device comprised of
      i) a moveable sample collection member having an analyte collection surface;
      ii) a storage medium wherein the storage medium comprises at least one stabilizing reagent that preserves at least one biological sample analyte for transport or storage; and
      iii) a storage medium holder having a means for holding the storage medium in a fixed position and a means for holding the moveable sample collection member;
      wherein the moveable sample collection holding means allows the moveable collection member surface to move between a first open position for collecting the biological sample on the analyte collection surface and a second closed position facing or contacting at least a portion of the storage medium;
   b) moving the moveable collection member surface to the first open position;
   c) first contacting the moveable collection member surface with the biological sample; and
   d) subsequently contacting the moveable collection member surface with the storage medium.

13. The method of claim 12 wherein the storage medium is removed from the storage medium holder after the moveable collection member surface is contacted with the storage medium.

14. The method of claim 12 wherein the stabilizing reagent comprises a weak base and a chelating agent.

15. The method of claim 12 wherein the stabilizing reagent comprises a chaotropic salt.

16. The method of claim 12 wherein the degradable biologically sourced analytes include nucleic acids, proteins, and respective fragments thereof.

17. The method of claim 12 wherein the biological sample is selected from the group consisting of saliva, blood, serum, lymph fluids, buccal cells, mucosal cells, cerebrospinal fluid, semen, feces, plasma, urine, a suspension of cells, or a suspension of cells and viruses.

18. The method of claim 12 wherein the storage medium holder releaseably holds the storage medium in the fixed position, allowing the storage medium to be separated from the storage medium holder.

19. The method of claim 12 wherein the analyte collection surface is absorbent.

20. The method of claim 12 wherein the device also comprises an identification label.

21. The method of claim 12 wherein the storage medium holder is dimensioned and configured to expose at least a portion of the storage medium for removal of the storage medium from the storage medium holder.

22. The method of claim 12 also comprising a sterility envelope surrounding the other device elements and those other elements are sterile and free from any biological sample analytes.

23. The method of claim 12 also comprising the step of manipulating the storage medium so as to remove at least a portion of the biologically sourced analyte present on the storage medium after the step of subsequently contacting the moveable collection member surface with the storage medium.

24. The device of claim 1 wherein the biological sample analyte comprises a nucleic acid or a fragment thereof.

25. The device of claim 1 wherein the biological sample analyte comprises a protein or a fragment thereof.

26. The device of claim 2 wherein the stabilizing agent comprises a surfactant.

27. The device of claim 2 further comprising uric acid or a urate salt.

28. The method of claim 12 wherein the biological sample analyte comprises a nucleic acid or a fragment thereof.

29. The method of claim 12 wherein the biological sample analyte comprises a protein or a fragment thereof.

30. The method of claim 14 wherein the stabilizing agent comprises a surfactant.

31. The method of claim 14 further comprising uric acid or a urate salt.

* * * * *